US010829598B2

(12) United States Patent
Ferreira et al.

(10) Patent No.: US 10,829,598 B2
(45) Date of Patent: Nov. 10, 2020

(54) PROCESS FOR PREPARING A POLYMER/BIOLOGICAL ENTITIES ALLOY

(71) Applicants: CENTRE NATIONAL DE LA RECHERCHE SCIENTIFIQUE-CNRS, Paris (FR); UNIVERSITE DE POITIERS, Poitiers (FR); VALAGRO CARBONE RENOUVELABLE POITOU-CHARENTES, Poitiers (FR)

(72) Inventors: Thierry Ferreira, Iteuil (FR); Frederic Bataille, Poitiers (FR); Cedric Dever, Poitiers (FR); Jacques Barbier, Poitiers (FR)

(73) Assignees: CENTRE NATIONAL DE LA RECHERCHE SCIENTIFIQUE-CNRS, Paris (FR); UNIVERSITE DE POITIERS, Poitiers (FR); VALAGRO CARBONE RENOUVELABLE POITOU-CHARENTES, Poitiers (FR)

( * ) Notice: Subject to any disclaimer, the term of this patent is extended or adjusted under 35 U.S.C. 154(b) by 0 days.

(21) Appl. No.: 15/220,159

(22) Filed: Jul. 26, 2016

(65) Prior Publication Data
US 2016/0333147 A1    Nov. 17, 2016

Related U.S. Application Data

(63) Continuation of application No. 14/308,526, filed on Jun. 18, 2014, now Pat. No. 9,428,744, which is a continuation-in-part of application No. PCT/FR2012/053014, filed on Dec. 20, 2012.

(30) Foreign Application Priority Data

Dec. 20, 2011  (FR) ...................... 11 62045
Feb. 29, 2012  (FR) ...................... 12 51852

(51) Int. Cl.
| *C08J 3/00* | (2006.01) |
| *C08J 3/20* | (2006.01) |
| *C12N 9/14* | (2006.01) |
| *C12N 11/04* | (2006.01) |
| *C08L 67/04* | (2006.01) |
| *C12N 9/20* | (2006.01) |
| *C12N 9/58* | (2006.01) |
| *C12N 11/18* | (2006.01) |
| *C12N 11/08* | (2020.01) |
| *C08K 5/00* | (2006.01) |

(52) U.S. Cl.
CPC ............. *C08J 3/005* (2013.01); *C08J 3/201* (2013.01); *C08J 3/203* (2013.01); *C08L 67/04* (2013.01); *C12N 9/14* (2013.01); *C12N 9/20* (2013.01); *C12N 9/58* (2013.01); *C12N 11/04* (2013.01); *C12N 11/08* (2013.01); *C12N 11/18* (2013.01); *C08J 2367/04* (2013.01); *C08J 2489/00* (2013.01); *C08K 5/0033* (2013.01); *C08L 2201/06* (2013.01); *C08L 2203/02* (2013.01); *C08L 2203/20* (2013.01)

(58) Field of Classification Search
None
See application file for complete search history.

(56) References Cited

U.S. PATENT DOCUMENTS

| 10,508,269 B2 | 12/2019 | Li et al. | |
| 2007/0225479 A1* | 9/2007 | Silvi | B29C 47/767 528/501 |
| 2007/0259195 A1* | 11/2007 | Chou | B32B 27/10 428/480 |
| 2011/0160335 A1 | 6/2011 | Cardinali et al. | |
| 2012/0184005 A1 | 7/2012 | Ferreira et al. | |
| 2017/0349723 A1 | 12/2017 | Ferreira et al. | |

FOREIGN PATENT DOCUMENTS

| CN | 1051188 A | 5/1991 |
| EP | 0 421 413 A1 | 4/1991 |
| EP | 2 325 255 A1 | 5/2011 |
| JP | H03179036 A | 8/1991 |
| JP | 4-168149 A | 6/1992 |
| JP | H11206370 A | 8/1999 |
| JP | 2002-362578 | 12/2002 |
| JP | 2002356623 A | 12/2002 |
| JP | 2006-036899 | * 2/2006 |
| WO | WO-2011/039489 A1 | 4/2011 |

OTHER PUBLICATIONS

Machine Translation of JP 2006-036899, Feb. 2006, p. 1-17.*
First Office Action for Japanese Patent Application No. 2014548158, dated Nov. 11, 2016 (English Translation).
Ebata et al., "Lipase-catalyzed transformation of poly (epsilon-caprolactone) into cyclic dicaprolactone," Biomacromolecules, Jan. 2000, pp. 511-514.

(Continued)

*Primary Examiner* — Robert T Butcher

(74) *Attorney, Agent, or Firm* — Salwanchik, Lloyd & Eisenschenk

(57) ABSTRACT

The present invention relates to a process for preparing a polymer/biological entities alloy, comprising a step of mixing a polymer and biological entities that degrade it, during a heat treatment, said heat treatment being performed at a temperature T above room temperature and said biological entities being resistant to said temperature T, characterized in that said biological entities are chosen from enzymes that degrade said polymer and microorganisms that degrade said polymer.

6 Claims, No Drawings

(56) References Cited

OTHER PUBLICATIONS

Yutaka et al., "Biodegradability of plastics," International Journal of Molecular Sciences, Sep. 2009, pp. 3722-3742.
Search Report for PCT/FR2012/053014, dated Apr. 12, 2013.
Written Opinion (English translation), International Application No. PCT/FR2012/053014, dated Apr. 12, 2013.
International Preliminary Report on Patentability (English translation), International Application No. PCT/FR2012/053014, dated Jun. 24, 2014.
Di Stasio, E. et al. "The effect of shear stress on protein conformation. Physical forces operating on biochemical systems: The case of von willebrand factor" *Biophysical Chemistry*, 2010, pp. 1-29, vol. 153, No. 1.
Thomas, C. R. et al. "Effects of shear on proteins in solution" *Biotechnol Lett*, 2011, pp. 443-456, vol. 33.
Ilo, S. et al. "Kinetics of Thermomechanical Destruction of Thiamin During Extrusion Cooking" *Journal of Food Science*, 1998, pp. 312-316, vol. 63, No. 2.

\* cited by examiner

US 10,829,598 B2

PROCESS FOR PREPARING A POLYMER/BIOLOGICAL ENTITIES ALLOY

CROSS-REFERENCE TO RELATED APPLICATIONS

This application is a continuation application of U.S. patent application Ser. No. 14/308,526 filed Jun. 18, 2014, which is a continuation in-part of International Patent Application No. PCT/FR2012/053014 filed Dec. 20, 2012, which claims the benefit of France Application No. 1251852 filed Feb. 29, 2012, which claims priority to France Application No. 1162045 filed Dec. 20, 2011, the entire disclosures of which are hereby incorporated herein by reference in their entireties.

BACKGROUND OF THE INVENTION

The invention relates to a process for preparing polymer materials derived from the petrochemical industry and/or biosourced, comprising in their composition biological entities chosen from enzymes and microorganisms enabling them to be degraded.

Polymer materials have been the subject of intensive use in recent years, in particular in the field of plastics. This intensive exploitation for common uses has been reflected by an accumulation of plastics in our environment, which is a source of visual nuisance, congestion of refuse sites and pollution of soils and marine media. Thus, as a result of their intrinsic properties, especially their resistance to degradation, the treatment of waste derived from these materials currently constitutes a real environmental and economic problem.

Several solutions have been proposed, among which are biodegradable plastic materials. Their formulation is in particular directed toward being adapted to degradation by microorganisms of the environment. However, this degradation generally takes place partially. In addition, it requires extremely favorable conditions detailed especially in standard EN 13432. These conditions are encountered under artificial conditions, such as industrial composts. For example, these materials are generally degraded at temperatures above 40° C. These temperature conditions are expensive to put in place, from an energy and also a financial point of view.

The standard alternatives for processing waste, such as incineration or dumping in a refuse site, prove to be detrimental even when they are applied to biodegradable polymer materials, since their degradation does not take place totally.

In addition, biodegradable materials have impaired physical properties, especially in terms of resistance to moisture, to temperature and to mechanical elongation. These deficiencies make them unsuitable for use in standard plastics processing operations such as injection molding or extrusion, and incompatible with the targeted applications.

Thus, these biodegradable materials, although promising, do not satisfy the requirements of industrialists and environmental requirements.

Materials consisting of polymers supplemented with a plant-based filler to improve the degradability of said materials have also been proposed. However, this degradation was due only to the degradation of said plant-based filler, which necessarily leads to a partial degradation. In addition, such a solution proved to be insufficient since it does not allow the mechanical properties of the polymer to be preserved. Such a material is thus also limited as regards its uses in the field of plastics processing.

There is thus a need for biodegradable materials, which have mechanical properties equivalent to those of plastics of petrochemical origin and which are suitable for use in the standard operations of plastics processing, said materials being able to be degraded totally, at an acceptable rate of degradation, and of doing so under temperature, pH and humidity conditions that are compatible with those generally encountered in the natural environment.

SUMMARY OF THE INVENTION

After long, in-depth studies, the inventors have developed a process for preparing polymer materials comprising in their composition biological entities that enable them to be degraded. The polymer materials, or polymer/biological entities alloys, thus obtained have physicochemical properties that enable total degradation under aqueous conditions while at the same time remaining stable under solid conditions.

The invention thus relates to a process for preparing a polymer/biological entities alloy, comprising a step of mixing a polymer and biological entities that degrade it during a heat treatment, said heat treatment being performed at a temperature T above room temperature and said biological entities being resistant to said temperature T, wherein said biological entities are chosen from enzymes and microorganisms that degrade said polymer. The inventors have shown, surprisingly and unexpectedly, that such a process allows the inclusion of biological entities into the very structure of the solid polymer, while at the same time maintaining an enzymatic activity or degrading activity of said biological entities.

Without wishing to be bound by theory, when said biological entities is an enzyme, the inventors put forward the hypothesis that the increase in temperature is accompanied by a vaporization of the hydroxyls of the polymer, making the enzyme active. Such an activation of the enzyme gives rise to a start of hydrolysis of the polymer and thus to vitrification coating said enzyme. The enzyme is then protected.

The inventors have also shown that the presence of the biological entities substantially improves the degradability of said alloy, and does so without impairing the mechanical properties of the polymer. Thus, the mechanical properties of said alloy are very similar, or even identical, to the mechanical properties of the polymer alone. These properties may be determined by means of measuring the resilience, the melt flow index, the tensile parameters such as the maximum tensile stress, the elongation at break or the tensile Young's modulus. Thus, the alloy obtained according to the process of the invention is highly suitable for the standard operations of plastics processing.

The inventors have shown, surprisingly, that the biological entities maintain its enzymatic activity in the alloy of the invention. In addition, said alloy remains stable when it is not in solution. The biological entities thus become active only when the alloy of the invention is placed in solution. Thus, the presence of these biological entities makes it possible to control the conditions and the rate of degradation of the alloy of the invention.

The alloys of the invention thus have the advantage of being stable when they are not placed in solution, which, on the one hand, facilitates the storage and transportation of the material, and, on the other hand, indicates the existence of a "release" effect (or delay effect) of the activation of the biological entities. Such a release effect is very advantageous since it makes it possible to control the activation of the enzymatic activity and of the degradation of the alloy of the invention.

The terms "polymer/biological entities alloy" and "alloy of the invention" mean a polymer comprising in its composition biological entities enabling degradation thereof. This expression thus encompasses polymer/enzyme alloys, polymer/microorganism alloys and polymer/enzyme/microorganism alloys. The term "biological entities" means an enzyme or a microorganism. In the context of the present invention, said biological entities has the feature of being able to degrade a polymer of interest.

The term "polymer/enzyme alloy" means a polymer comprising in its composition enzymes enabling degradation thereof. Preferentially, said polymer is a biodegradable polymer. The use of a biodegradable polymer as starting material for performing the process makes it possible to obtain a polymer/enzyme alloy with more advantageous degradation properties.

The term "polymer/microorganism alloy" means a polymer comprising in its composition microorganisms enabling degradation thereof. Typically, these microorganisms produce enzymes that degrade said polymer.

The term "heat treatment" means all polymer transformation operations during a raising of the temperature of said polymer, preferentially to a temperature above room temperature, and more preferentially to a temperature above 50° C. Preferentially, said heat treatment allows the inclusion of the biological entities. More preferentially, said heat treatment consists of an operation chosen from extrusion, injection-molding, thermoforming, rotary molding, compression, calendering, ironing, coating, stratification, expansion, pultrusion, extrusion blow-molding, extrusion-swelling and compression-granulation. These operations may be performed on polymers in liquid and/or solid form. In a preferred embodiment, the polymer is in solid form. In another embodiment, said polymer is in syrup form.

The term "resistant to a temperature" in connection with a biological entity means that said biological entity exhibits an enzymatic/degrading activity after a heat treatment at this temperature.

In the context of the invention, the term "maintaining the enzymatic activity" means maintaining any degrading activity of the biological entities, enabling a degradation of the polymer. In particular embodiments, the degrading activity of the biological entities in the alloy may be increased or decreased compared to their degrading activity before the heat treatment.

The term "room temperature" generally means a temperature of between 20° C. and 30° C., and more preferentially a temperature of about 25° C.

The term "extrusion" means the preparation of a polymer in a desired form, from a material in the form of granules or powder, using an extruder. This term encompasses profiled extrusion, extrusion blow-molding, extrusion-swelling and extrusion-calendering.

This extrusion step takes place at the melting point of said polymer. The polymer is then in a partially or totally molten state. This temperature thus depends on the nature of said polymer and the nature of the biological entities of interest. This temperature may be readily determined by a person skilled in the art, in the light of his general knowledge. Under the action of the temperature and the pressure, said biodegradable polymer in molten or partially molten form mixes with the other starting materials, and especially the biological entities that degrade it. Preferentially, said temperature T is between the glass transition temperature and the melting point of said polymer. More preferentially, said temperature T is the melting point of said polymer. Typically, said temperature T depends on the nature of said polymer and the nature of the biological entities of interest and is greater than 50° C., preferentially greater than 60° C., preferentially greater than 70° C., preferentially greater than 80° C., preferentially greater than 90° C., preferentially greater than 100° C., preferentially greater than 120° C., preferentially greater than 140° C., preferentially greater than 150° C. Typically, this temperature T does not exceed 300° C.

The main function of the extruder is to enable, via the action of the temperature and the pressure, the passage of the polymer through a die which is at its end. Typically, an extruder is composed of one or more heating sheaths having different temperature levels, one or two Archimedean screws for transporting the material along the sheath, a hopper for feeding into different points material to be extruded, which is in the form of granules or flour, a more or less complex die which is at the end of the sheath and which gives the desired shape and size to the plastic material emerging continuously. Preferentially, the extrusion step is performed using an extruder of BC21 twin-screw type, sold under the name Clextral.

The use of this extrusion step falls within the normal competence of a person skilled in the art. It generally takes place according to the following steps:
 introduction of a mixture of polymer and of biological entities that degrade it;
 passage of said mixture into the extruder;
 output of a rod through a die;
 cooling of said rod, optionally followed by drying;
 chopping in the form of regular granules as a function of the desired form; and
 drying, preferentially in a rotary oven, at a temperature of between about 40° C. and about 60° C., and even more preferentially at a temperature of about 50° C.

Typically, the biological entities/polymer weight ratio is between about 0.1% and about 10%, preferentially between about 0.5% and about 8%, preferentially between about 1% and about 6%, preferentially between about 1% and about 5%, preferentially between about 1% and about 4%, preferentially between about 1% and about 3%, preferentially between about 1.5% and about 3%, and even more preferentially this ratio is about 2%. This ratio is adapted by a person skilled in the art as a function of the nature of the biodegradable polymer, the nature of the biological specifies used, and the desired results, especially in terms of degradability of the alloy obtained via the process.

It is an object of the invention to provide a process for preparing a polymer/biological entities alloy, comprising a step of mixing a polymer and biological entities, said biological entities being chosen from enzymes and microorganisms that degrade said polymer, wherein said alloy is prepared during a heat treatment performed at a temperature T above room temperature, at which the polymer is in a partially or totally molten state, and wherein said biological entities are able to degrade said polymer in said alloy. Preferentially, the process of the invention also comprises the addition of a substance that can optimize the degradation capacities of said biological entities. Typically, when said biological entities are enzymes, these substances may be cofactors for said enzymes, such as divalent cations.

In the context of the present invention, the term "polymer" covers polymers derived from the petrochemical industry, biosourced polymers and bio-based polymers.

In a particular embodiment, the polymers that are relevant in the context of the present invention are derived from the petrochemical industry. The advantage of these polymers is the control of the polymerization process and of the base constituents, which makes make it possible to ensure easy transformation. Typically, they are polymers containing monomer units comprising hydrolyzable bonds, for instance esters or amides.

A non-limiting list of these monomers consists of caprolactone, tetramethylene succinate, esters, esteramides, propylene, $C_1$-$C_6$ hydroxyalkanoates and butylene adipate-co-terephthalate.

A non-limiting list of polymers that are relevant for performing the invention consists of polycaprolactone, polytetramethylene succinate, copolyesters, polyesteramides, polypropylene, vinyl polymers, poly($C_1$-$C_6$ hydroxyalkanoates) and poly(butylene adipate-co-terephthalate), cellulose acetate, poly(butylene succinate) and polyamides, and mixtures thereof.

Typically, said polyamides are aliphatic polyamides chosen from:
  polycaprolactam (PA6),
  polylauroamide manufactured by opening of the lauryl lactam ring (PA12),
  polyundecanamide manufactured from amino undecanoic acid (PA11),
  polytetramethyleneadipamide manufactured from tetramethylenediamine and adipic acid (PA 4-6),
  polyhexamethylene adipamide (PA6-6),
  polyhexamethylenenonanediamide manufactured from hexamethylenediamine and 1,9-nonanedioic acid (PA 6-9),
  polyamide 6.6, sebacic acid-1,6-hexanediamine manufactured from hexamethylenediamine and sebacic acid (PA6-10), and
  polyhexamethylenedodecanediamide manufactured from hexamethylenediamine and 1,12-dodecanedioic acid (PA6-12).

Preferentially, said polyamide is polyundecanamide manufactured from amino undecanoic acid (PA11).

In another mode of the invention, the polymers that are relevant in the context of the present invention are biosourced polymers.

The term "biosourced polymer" means a polymer derived from renewable resources. These biosourced polymers are occasionally used in combination with additives such as plasticizers. Among these biosourced polymers, biodegradable biosourced polymers are differentiated from nonbiodegradable biosourced polymers such as:
  polyamides, especially polyamide PA11;
  polyvinyl chloride;
  polyethylene; and
  polypropylene.

Preferentially, said polymer is chosen from polycaprolactone (or CAPA), polylactic acid, polyethylene terephthalate, poly(trimethylene terephthalate), a $C_1$-$C_6$ polyhydroxyalkanoate, cellulose acetate, poly(butylene adipate-co-terephthalate), poly(butylene succinate) and polyamide PA11 and mixtures thereof.

More preferentially, said polymer is polylactic acid or PLA. PLA has mechanical properties similar to certain petrochemical thermoplastics such as polypropylene.

Even more preferentially, said polymer is polycaprolactone or CAPA.

In another embodiment, said polymer is a bio-based polymer. The term "bio-based polymer" means a polymer manufactured using a compound of natural origin, preferentially of non-petrochemical origin.

In the context of the present invention, a biological entities should be chosen, preferentially an enzyme, which withstands the operating temperature of the extrusion step according to the process of the invention. A person skilled in the art has general knowledge enabling him to determine these temperatures and to identify biological entities that withstand these temperatures.

The term "biodegradable polymer" means a material that can be degraded by biological entities. The result of the degradation of such materials is the formation of water, carbon dioxide and methane, and optionally byproducts. The byproducts obtained during the degradation of said polymers are nontoxic.

Standard EN 13432:2000 states the requirements relating to packaging that is upgradable by composting and biodegradation. It sets the characteristics that a material should have in order to be defined as compostable. It is based on the following criteria:
  The biodegradability: it is measured by the metabolic conversion of the material into carbon dioxide. This property is measured using the standardized method EN 14046. The degree of decomposition to be achieved is 90% in less than 6 months.
  The disintegration: this is the fragmentation of the material and its absence of visual identification in the final compost. It is measured by the composting method EN 14045. The material should be disintegrated in the presence of organic waste in less than three months. After this time, the compost is screened on a 2 mm screen. The residues of the material greater than 2 mm in size are considered as undisintegrated. This fraction should represent less than 10% of the initial mass.
  A low content of heavy metals and the absence of negative effects on the quality of the compost: a plant growth test is performed, according to the method OECD test 208, with a sample of compost. Other physicochemical parameters of the compost should not be modified (relative to a compost not containing polymers): salinity, % of nitrogen, phosphorus, magnesium and potassium.

DETAILED DESCRIPTION

In a first preferred embodiment, said biological entities are enzymes, preferentially enzymes that are resistant to the extrusion temperature.

The term "enzymes that are resistant to the extrusion temperature" means enzymes whose protein structure and/or enzymatic activity are not affected by the temperature at which the extrusion step according to the process of the invention is performed. According to the invention, the degrading activity of the enzymes may decrease but said enzymes remain able to depolymerize the polymer in the alloy. These enzymes are thus highly suitable for use at temperatures above room temperature.

Preferentially, said enzymes are chosen from heat-resistant enzymes and heat-stabilized enzymes.

The term "heat-resistant enzymes" means enzymes whose intrinsic nature affords resistance to high temperatures, in particular to the temperature at which the extrusion step according to the process of the invention is performed. More particularly, a heat-resistant enzyme still exhibits a degrading activity after the extrusion step according to the process of the invention, so that said enzyme is able to degrade the polymer in the alloy.

Preferentially, said heat-resistant enzymes are chosen from lipase PS from *Pseudomonas cepacia*, lipase AK from *Pseudomonas fluorescens*, lipase B from *Candida antartica*, proteinase K, a $C_1$-$C_6$ polyhydroxyalkanoate depolymerase, and mixtures thereof.

The term "heat-stabilized" or "heat-protected" enzymes means enzymes which are not naturally heat-resistant, but which are in a particular form that gives them resistance to the temperature at which the extrusion step according to the process of the invention is performed. Preferentially, these heat-stabilized enzymes are obtained via a chemical or physical process.

Preferentially, said heat-stabilized enzymes are chosen from enzymes encapsulated in nanocapsules consisting of the same material as said polymer, enzymes encapsulated in cage molecules and enzymes aggregated together.

These heat-stabilized enzymes may be obtained by encapsulation of the non-heat-resistant enzymes in nanocapsules, preferentially in nanocapsules consisting of the same material as said polymer. The encapsulation techniques are well known to those skilled in the art. Typically, this encapsulation is performed by using nanoemulsions. This encapsulation of the enzymes makes it possible to control the activation of the enzymes. This embodiment of the invention is particularly advantageous for a use of the alloys of the invention in the wrapping of food products.

These heat-stabilized enzymes may also be obtained by encapsulation of the enzymes in cage molecules. Such an encapsulation makes it possible to protect said enzymes from any temperature-related degradation.

The term "cage molecule" means a molecule that can be inserted into the structure of said enzymes to stabilize them and to make them resistant to temperatures above room temperature.

These heat-stabilized enzymes may also be obtained by aggregating non-heat-resistant enzymes together. A person skilled in the art has sufficient technical knowledge to perform such an aggregation.

In a particular embodiment, said enzymes are in the form of apoenzymes, and are activated in the presence of cofactors.

In a second embodiment, said biological entities are microorganisms.

Typically, these microorganisms are microorganisms that may or may not be capable of sporulating and producing enzymes that degrade polymers of interest. Preferentially, these microorganisms are bacteria, fungi or yeasts. In the context of the invention, the term "microorganism" also includes spores.

In one embodiment, the alloy of the invention is a polymer/microorganism alloy, preferentially a polylactic acid/microorganism alloy.

Preferentially, said microorganisms are chosen from bacteria of the genus *Ochrobactrum*, bacteria belonging to the phylum of firmicutes (*Firmus cutis*), bacteria of the class of bacilli, especially the bacterial strains *Bacillus cereus* spp. and more particularly *Bacillus cereus* G9241, and the bacterial strains *Bacillus clausii* spp.

More preferentially, said microorganism is a bacterial strain of the genus *Ochrobactrum*, known as *Ochrobactrum* sp. 37S and deposited according to the Treaty of Budapest on 23 Jul. 2009 in the name of the Centre National de la Recherche Scientifique at the Collection Nationale de Cultures de Microorganismes under the number CNCM 1-4212, or a variant of said strain, said variant being capable of degrading polylactic acid.

Preferentially, said polymer is polylactic acid and said biological entity is *Ochrobactrum* sp. 37S bacteria. Typically, said bacteria degrades polylactic acid.

The term "variant" means:

a natural variant of a strain according to the invention, i.e. a variant obtained spontaneously from a strain according to the invention after incubation in a selection medium. A natural variant is thus obtained without any genetic manipulation by the operator, but only by natural mutation of the strain and selection of this mutated strain in a suitable medium, or a variant of a strain according to the invention comprising at least one mutation in its genome, said mutation being induced by genetic engineering, for example by site-directed mutagenesis or random mutagenesis. For example, random mutagenesis may be performed using mutagens such as radiations (UV rays, ionizing radiations, heat) or chemical compounds (nitrous acid, ethyl methanesulfonate, N-methyl-N'-nitro-N-nitrosoguanine, N-ethyl-N-nitrosourea, acridine orange, proflavin, etc.).

The term "mutation" means the addition, deletion or substitution of at least one nucleotide in the genome of the strain according to the invention.

In another embodiment, the alloy of the invention is a polymer/spores alloy, such as a polylactic acid/spores alloy. In a particular embodiment, the spores are spores of *Bacillus licheniformis*. Thus, the invention relates to a process for preparing a polymer/biological entities alloy, comprising the following steps:

i) selection of a polymer, preferentially a biodegradable polymer;

ii) selection of biological entities which are capable of degrading said polymer and which are resistant to a temperature T above room temperature; and iii) mixing of said polymer and of said biological entities during a heat treatment performed at the temperature T, characterized in that said biological entities are chosen from enzymes that degrade said polymer and microorganisms that degrade said polymer.

The invention also relates to a process for preparing a polymer/biological entities alloy comprising a step of extruding a polymer with biological entities selected from the group consisting of enzymes and microorganisms that degrade said polymer, wherein the biological entities/polymer weight ratio is between about 1% and 5%, the step of extrusion being performed at a temperature at which the polymer is in a partially or totally molten state.

All the features described previously apply to this process.

The process has the advantage of being compatible with the standard equipment used in the plastics processing industry, which enables its rapid and direct implementation by professionals, without significant modification of the production tools conventionally used, especially those ordinarily reserved for the production of plastics of petrochemical origin.

In addition, the process of the invention does not require the use of products that are potentially hazardous to human health or to the environment. Nor does it generate any byproducts that may represent such a hazard.

The process of the invention makes it possible to obtain a "tailor-made" polymer/biological entities alloy by including biological entities, preferentially enzymes, with a polymer, preferentially a biodegradable polymer, which conditions the degradation of the alloys thus obtained.

The invention thus makes it possible to obtain a polymer/biological entities alloy, preferentially a sole polymer/enzyme alloy for which it is possible to control the rate of degradation.

A non-limiting list of these polymer/enzyme alloys consists of polycaprolactone/lipase PS from *Pseudomonas cepacia*; polycaprolactone/lipase B from *Candida antartica*; polylactic acid/proteinase K;

$C_1$-$C_6$ polyhydroxyalkanoate/$C_1$-$C_6$ polyhydroxyalkanoate depolymerase couples.

Preferentially, the invention relates to a process for preparing a polymer/enzyme alloy, comprising the extrusion of polycaprolactone with a lipase, preferentially amanolipase PS from *Pseudomonas cepacia*, at the melting point of polycaprolactone in an enzymes/polymer ratio of 2% by weight. Specifically, the inventors have demonstrated that the alloy thus obtained degrades totally after 4 months in aqueous medium, whereas polycaprolactone not supplemented with lipase does not degrade within this time period.

The inventors have also shown and exemplified that such an alloy degrades at extrusion temperatures of 80° C., 100° C., 120° C. and 140° C.

In a preferred embodiment, the invention also relates to a polymer/enzyme alloy, characterized in that said enzymes degrade said polymer and that they are heat-stabilized.

These alloys are highly advantageous due, firstly, to their improved degradability when they are placed in aqueous solution, and, secondly, to their mechanical properties adapted to their uses in industry. The inclusion of the enzyme into the alloy does not impair the properties of the polymer alone. Thus, the mechanical properties of said alloy are very similar, or even identical, to the mechanical properties of the polymer alone.

Preferentially, said heat-stabilized enzymes are chosen from enzymes encapsulated in nanocapsules consisting of the same material as said polymer, enzymes encapsulated in cage molecules and enzymes aggregated together.

All the technical features mentioned previously concerning said polymer and said heat-stabilized enzymes are applicable to this alloy.

Alternatively, the invention relates to a polymer/biological entities alloy characterized in that said polymer is polylactic acid and said biological entities are *Ochrobactrum* sp. 37S bacteria, said bacteria degrading polylactic acid.

In another aspect, the invention relates to the use of the polymer/biological entities alloy of the invention in the sectors of agriculture, horticulture, packaging, catering, the environment, transport, textiles, electronics and pharmacy. Hereinbelow, the terms "alloy of the invention" and "polymer/biological entities alloy obtained according to the process of the invention" are used without discrimination.

Preferentially, the invention relates to the use of the alloy of the invention in the packaging sector, more preferentially for packaging food products, especially fruit and vegetables, and in the bakery sector. Thus, the invention relates to the use of the alloy of the invention as a food packaging with a long shelf life. Specifically, the alloy of the invention is highly suited to coming into contact with food products since it does not have any harmful effects, it is readily degradable and it constitutes a barrier to the passage of carbon dioxide, oxygen and water, thus preventing the impairment of foods.

The invention also relates to the use of the alloy of the invention in the agriculture sector, especially for obtaining granules comprising plant-protection products, mulching films, tunnel films and tying-up materials.

The invention also relates to the use of said alloy for obtaining bottles.

Finally, the invention relates to the use of the alloy of the invention in the medical field, especially for producing resorbable sutures and as a therapeutically active molecule vector. Preferentially, these alloys are used in the form of nanoparticles containing said therapeutically active molecule. A person skilled in the art has the general technical knowledge enabling him to prepare nanoparticles from the alloy according to the invention.

The advantage of using the alloys of the invention in therapy is obvious in several respects. Firstly, the degradation of the nanoparticle makes it possible to deliver the medicament gradually to the target cells. In addition, it makes it possible to limit the side effects associated with the accumulation of the therapeutic molecule in certain tissues, such as the detoxification organs such as the liver and the kidney. Finally, the biodegradability of such nanoparticles limits the potential environmental impacts, which are associated with the spreading of the nanoparticles into the external medium via the natural secretions of the patient.

The process for preparing the alloys according to the invention makes it possible to obtain alloys whose degradability is suited to the desired use. Thus, in a therapeutic context, a person skilled in the art will be capable of adapting the process to obtain a alloy that does not entail any accumulation of nanoparticles in certain organs of the treated patient, so as to be able to avoid the adverse effects that may be associated with the presence of said nanoparticles.

A person skilled in the art will also have to adapt the nature of the therapeutically active molecule encapsulated by the nanoparticle of the invention as a function of the type of pathology to be treated and of the nature of the nanoparticle per se. Specifically, depending on the physicochemical properties of said nanoparticle (especially its weight, its size, its lipophilicity, its hydrophilicity and its state of ionization), it may or may not be able to cross the transmembrane barrier. Thus, the nature of the nanoparticle has an influence on the distribution of the therapeutically active molecule in the individual to whom the nanoparticle consisting of the alloy of the invention is administered.

EXAMPLES

Example 1

Preparation of Polymer/Enzyme Alloys According to the Invention

Materials and Methods
1. Inclusion of Enzymes into the Starting Material During the Extrusion Step The incorporation of enzymes into the starting biodegradable polymer is performed during the "extrusion" step.

The extrusion step is performed using an extruder of BC21 twin-screw type of Clextral brand (motor power 9 kW, maximum screw speed 600 rpm, maximum current 18.9 A). The screws have a diameter d of 25 mm and the separation between the two screws is 21 mm. The length of the sheath is 600 mm, i.e. a ratio L/d of 24.

The extrusion takes place in 5 steps:
1. introduction of a biodegradable polymer/enzymes mixture,
2. passage of said mixture into the extruder,
3. output of a rod through a circular die 3 mm in diameter, 4. cooling of the rod in a bath of cold water three meters long, followed by "drying" with pulsed cold air,
5. cutting in the form of regular granules by a system with a rotating knife.

The formulations may vary as a function of the biodegradable polymer/enzymes ratio. In the experiments presented in the present patent application, the results correspond to a ratio of 2% (m/m) of enzyme in the material.

The granules obtained by extrusion are then dried in a rotary oven at 50° C. for 15 hours (rotary mixer equipped with a jacket with circulation of oil) so as to remove the residual water present, due to the passage into the tank of water. The monitoring of the moisture content during the drying is performed by means of a moisture analyzer equipped with infrared resistances.

2) Preparation of the Specimens—Injection-Molding

In order to evaluate the mechanical properties of the polymer/enzyme alloy obtained, and also its degradation capacities, molded pieces of standard format, referred to as "specimens", are obtained by injection-molding.

Injection-molding is a batch process for putting in form granules of three-dimensional finished products. The principle consists in heating the plastic material in the feed sheath to bring it in the molten state to the assay and compression zone in order to inject it into the mold via a piston. The molded piece is cooled in the mold, and then ejected.

The injection press used is of the Arburg brand, Allrounder 1000-420C-250 model.

The injection-molded specimens correspond to type 1 of standard ISO 3167.

Result

1. Selection of the Enzymes in Liquid Medium

For the implementation of the process, enzymes capable of degrading the biodegradable polymer should be identified, so as to identify the appropriate enzymes/material "couple" that will be used during the extrusion step.

We developed two simple tests in order to identify the enzymes of interest. These tests are performed on samples of pure material in specimen or granule form, respectively.

The tests presented hereinbelow were performed on specimens or granules of polycaprolactone or CAPA (Perstorp; Ref. 6506; 50 000 g/mol). The inventors evaluated two commercial enzymes, known for their capacity to degrade CAPA: Lipase PS from *Pseudomonas cepacia* and lipase AK from *Pseudomonas fluorescens* (Amano, Japan).

a) Tests on Specimens

The specimens of raw polymers placed under biodegradation conditions are specimens derived from the injection-molding of CAPA granules. All the biodegradation tests proceed in an oven thermally regulated at 30° C.

The tests presented in this study were performed in a nutrient solution, the composition of which is defined according to standard ISO 14852: 1999. Alternatively, the degradation may also be evaluated in Fontaine Cristalline brand water, i.e. a mineral water of constant composition making it possible to have the same medium conditions.

For these tests, the specimens are maintained fully immersed in the solution, which is optionally supplemented with enzymes at a final concentration of 200 mg/L.

The monitoring of the degradation of the materials is performed by calculating the loss of mass of the sample after a defined time of presence in the medium.

This method uses a series of 13 identical specimens, five of which are oven-treated at 103° C. for 48 hours in order to determine the water loss of the sample. This step makes it possible to perform a correction for the calculation of the loss of mass of the samples placed in biodegradation. The other 8 specimens are immersed in the degradation medium and placed in an oven thermally regulated at 30° C. They are then withdrawn after a defined time in order to monitor the behavior of the material over time. After each withdrawal, the specimens are dried in the oven at 103° C. for 48 hours and weighed.

The loss of mass is calculated according to the following formula:

$$\Delta m = \frac{(m_i - m_f)}{m_i} * 100 - \Delta m \text{ between room temperature and } 103° \text{ C.}$$

With
  $m_i$: initial mass of the specimen
  $m_f$: final mass of the specimen

The results show that the presence of lipase from *Pseudomonas fluorescens* does not make it possible to improve the biodegradability of polycaprolactone since the degree of degradation is substantially the same as when the enzymes are not present.

On the other hand, with regards the lipase from *Pseudomonas cepacia*, a very marked difference is observed from the very first withdrawal performed after 7 days of contact with the medium. Specifically, a degree of degradation of 5% is obtained, whereas over the same time, the sample degraded in the absence of enzyme shows a loss of mass of only 0.2%.

Nevertheless, a steady stage is rapidly observed and the degree of biodegradation no longer changes. It was therefore decided to change the nutrient solution supplemented with enzymes (still at 200 mg/L of nutrient solution). This change was made 44 days after the start of the degradation. This made it possible to observe a resumption of degradation up to about 9% in 70 days.

b) Tests on Granules

The advantage of this method is that it makes it possible to work on small reaction volumes, making the experiments substantially less expensive. Furthermore, several enzymes and several concentrations can be tested simultaneously. Finally, the possibility of working with high concentrations of enzymes makes it possible to obtain high degrees of degradation over short times.

In this experiment, the CAPA granules (approximate volume: 50 mm$^3$; approximate mass: 40 mg) were incubated in 1.9 ml of a buffer (25 mM phosphate buffer, pH 7, sodium azide 2 g/L), optionally supplemented with lipase PS from *Pseudomonas cepacia* at a final concentration of 20 mg/ml. The incubation is performed at 28° C. At regular time intervals, the granules are withdrawn, rinsed thoroughly with water and then incubated for 24 hours at 28° C. for drying. The mass is then determined and compared with the starting mass, i.e. before incubation in the reaction medium.

The results show a degree of degradation of the CAPA of more than 50% with lipase PS from *Pseudomonas cepacia*, under the stated conditions, confirming the results obtained with the specimens.

This protocol may be used for the determination of the most relevant enzyme for the purpose of its subsequent inclusion into a given polymer.

Furthermore, it may also make it possible to identify certain "additives" which may have the property of optimizing the degradation activity. These additives may then be added with the enzyme to the material during the extrusion step, to accelerate the degradation thereof.

2. Evaluation of the Heat Resistance of the Enzymes in Order to Determine the Optimum Extrusion Temperature During the extrusion step, the polymer/enzyme mixture is subjected to a high temperature corresponding to the melting point of the polymer. In the case of CAPA, we set this extrusion temperature at 80° C. According to the supplier's technical sheet, lipase PS from *Pseudomonas cepacia* is stable in powder form for several hours at 100° C.

However, these data refer to the lipase activity of the enzyme and do not evaluate the heat resistance of its CAPA depolymerase activity.

We therefore performed the experiment on granules described above, but treating the enzymatic solution (20 mg/ml of enzyme) for 5 minutes at 80° C. The time and temperature selected correspond to thermal conditions close to those encountered during the extrusion step.

The results show that this treatment has a low impact on the CAPA depolymerase activity of the enzyme. Specifically, the inventors revealed only a 10% loss of activity at 7 days. It follows that lipase PS from *Pseudomonas cepacia* is an excellent candidate for preparing the CAPA/enzyme alloy.

3. Incorporation of Lipase PS from *Pseudomonas cepacia* During the Polycaprolactone Implementation Process The inventors thus performed an extrusion of polycaprolactone incorporating said enzyme. To do this, a mixture of polymer in powder form and of enzyme in powder form is placed in a metering device.

In the experiments that are presented herein, the flow rates of these two metering devices were adjusted so as to obtain a percentage of enzyme in the material of 2% (m/m). A formulation without enzyme was also prepared (control) (Table 1).

TABLE 1

Formulations prepared in this study

| Formulation (mass %) | Mass of enzyme (g) in the metering device | Mass of CAPA 6506 P (g) in the metering device |
|---|---|---|
| 98 m % CAPA 6506 + 2 m % lipase | 30 | 1500 |
| 100 m % CAPA 6506 | 0 | 1500 |

The extrusion was performed at 80° C., so as to have a temperature above the melting point of CAPA (60° C.), but not too high, so as to avoid any risk of denaturing the enzyme.

The precise parameters of the extrusion, which was performed under the same conditions for the two formulations, are presented in Table 2.

TABLE 2

Parameters of the extrusions performed in this study

| Formulation | Extrusion temperatures (zone 1 at die) | Speed BC 21, T/min | Pressure, bar | Torque (%) |
|---|---|---|---|---|
| 98 m % CAPA 6506 + 2 m % lipase | 18/20/39/65/67/72/68/65/71 | 256 | 71-74 | 53-54 |
| 100 m % CAPA 6506 | 20/20/40/65/65/69/65/65/65 | 256 | 73-75 | 55-60 |

The term "torque" cited in table 2 corresponds to the relative motor intensity and represents the mechanical energy supplied by the extruder to the extruded material.

The granules obtained were then dried in a rotary oven in order to remove the residual water.

The two formulations then underwent an injection-molding step for the purpose of obtaining normalized specimens. The injection-molding conditions were identical for the two materials.

Table 3 shows the settings of the injection press that were used in this study.

TABLE 3

Injection-molding parameters on an Arburg 100/420C/250 press

| | |
|---|---|
| Temperatures ° C. (Feed → Nozzle) | 40/55/60/80/110 |
| Imprint | Specimen |
| Assay speed (v401) m/min | 8.0 |
| Assay volume (V403) cm$^3$ | 14.3 |
| Counterpressure (p401) bar | 150 |
| Assay time (t402M) s | 3.9 |
| Injection pressure (p301) bar | 800 |
| Injection flow rate (Q301) cm$^3$/s | 5 |
| Switching (V311) cm$^3$ | 5 |
| Maintenance pressure (p321) bar | 650 |
| Maintenance flow rate (Q321) cm$^3$/s | 5 |
| Maintenance time (t321) s | 30 |
| Cooling time (t400) s | 25 |
| Cycle time (t902M) s | 65.8 |
| Mattress (V321I) s | 1.3 |
| Ejector speed (v602) mm/s | 10 |
| Ejector force (F601) kN | 5 |
| Nozzle position | Detached |
| Mold temperature ° C. | 18 |

The degradation efficacies were evaluated in *Cristalline* mineral water. Briefly, for each formulation, four normalized specimens (whose masses were measured beforehand) were immersed in a tank of water (*Cristalline* reference mineral water). The tanks were then placed in a chamber thermally regulated at 32° C. and ventilated.

A specimen was then withdrawn after 1, 2, 3 and 6 months and weighed (after oven treatment at 103° C. for 48 hours). The degradability of the material was measured by means of the loss of mass, calculated as stated previously.

The results obtained show a total biodegradability of CAPA when the enzyme was incorporated into the material, at and above 102 days of incubation of the specimens in water, this demonstrating that the enzyme withstood the heat treatments inflicted during the extrusion and injection-molding steps.

The inventors have thus shown that an enzyme can effectively be incorporated into a polymer from the extrusion phase while at the same time maintaining the degradation properties of the polymer.

This approach thus constitutes a simple method, which is easy to implement and which can be readily adapted to other polymer/enzyme couples for controlling the degradation of materials in natural medium.

Example 2

Characterization of the Alloys of the Invention

The inventors compared the mechanical properties of CAPA alone, of CAPA mixed with a plant-based charge and of a alloy consisting of CAPA and lipase PS from *Pseudomonas cepacia* and obtained according to the process of the invention.

Materials and Methods
1. Production of the Alloys

The CAPA/lipase PS from *Pseudomonas cepacia* alloy was obtained using the following starting materials:

TABLE 4

Starting materials used for the formulation of the alloys

| Name | Supplier | Definition |
|---|---|---|
| CAPA 6506 (CAPA) | Solvay | Polycaprolactone powder |
| Wheat | Amo | Native wheat flour reference "La Doree" predried |
| Lipase | Amano | Reference "PS SD" |

Step of Granulation by Extrusion

The extrusion step was performed in five steps, using a Clextral BC21 co-rotating twin-screw extruder
- introduction of the various elements in the envisaged proportions by means of a weight-metering device and a volumetric metering device;
- melting, kneading, degassing, mixing and placing under pressure of the material in the successive parts of the extruder;
- output of a rod through a circular die 3 mm in diameter;
- cooling of the rod in a tank of cold water three meters long, followed by "drying" with pulsed cold air;
- cutting in the form of regular granules by a system with a rotating knife.

Four formulations were thus prepared (the percentages correspond to mass percentages):
100% CAPA;
98% CAPA+2% lipase;
80% CAPA+20% wheat;
55% CAPA+45% wheat.

The addition of a plant-based charge (wheat flour) is a standard alternative for increasing the degree of degradation of a polymer. Specifically, the maximum degree of degradation corresponds to the degradation of the plant-based charge, the polymer used as binder not in fact being degraded (see hereinbelow).

The granules obtained by extrusion were then dried in a rotary oven at 40° C. for 12 hours so as to remove the residual water present, due to the passage into the tank of water. The dried granules were then able to be injection-molded and characterized.

Injection-Molding Step

The injection-molding step makes it possible to transform the granules obtained by extrusion into characterization specimens. The principle of the injection molding consists in heating the plastic material in a sheath to melt it (plasticization phase) and inject it under pressure into a mold by means of a piston. The material is solidified and partly cooled in the mold, before being ejected. The press used is an Arburg brand press of Allrounder 1000-420C-250 model.

The injection-molded specimens correspond to type 1 of standard ISO 3167.

Certain "97% CAPA+2% lipase" specimens obtained by injection-molding underwent a post-treatment before characterization, consisting of storage in a sealed zip-lock bag placed in a closed cardboard box for 1 month at room temperature, the object of this step being to evaluate the impact of storage on the stability of the material, both from the point of view of its mechanical properties and of its capacity to be degraded.

2. Determination of the Mechanical Properties

Tensile Test

The tensile properties are determined according to the recommendations described in International standard ISO/R 527 (determination of the tensile properties). These tests should be performed under well-defined conditions as regards temperature, humidity and speed of separation of the jaws.

The tensile test consists in imposing an elongation onto a specimen of initial cross section So and of useful length Lo. The specimen is fitted at its two ends into jaws. One of these jaws, which is mobile, is connected to a drive system at a linear speed of travel. The measurement of the work is performed using an electronic force sensor (10 kN).

Three items of information are noted from these tests:
the maximum tensile stress (Cmax TR; MPa),
the elongation at break (in %),
the tensile Young's modulus (in MPa).

As indicated in the standard, the tests are performed on five specimens of each batch of material and the results presented are the mean of these five determinations. The speed of displacement is set at 50 mm/min and the tensile modulus is calculated between 10% and 50% of the maximum stress value. The tensile testing machine used is sold by Zwick.

Charpy Impact

This method makes it possible to study the behavior of defined specimens, subjected to impact stresses to estimate the fragility or strength thereof. For these tests, the inventors used the specimens of type 1 described previously, unnotched.

The equipment used is an impact pendulum with an energy of 15 joules of the Zwick brand. The unit is driven by software which records the values measured and the analyses. During the test, the specimen is placed horizontally before the supports and hit with the pendulum at its center. The Charpy impact resistance corresponds to the energy absorbed by the breaking of a specimen relative to its cross section before the test (resilience).

3. Rheological Properties: Melt Flow Rate (MFR)

Standard ISO 1133 prescribes a method for determining the melt flow rate (or MFR) of thermoplastics under defined temperature and pressure conditions. This test makes it possible to determine the grade of the polymer tested and gives information regarding the capacity of the polymer to flow through a die for a given temperature (which is an important parameter for injection molding).

The apparatus used is a Zwick brand extrusion plastometer connected to a precision balance and driven by specific software capable of determining the MFR expressed in g/10 minutes.

During a test, the mixture, heated in the vertical cylinder, is extruded through the die using a charge attached to a piston. Five extrudates are cut at regular time intervals, recovered and then weighed. The parameters to be set are thus the temperature of the cylinder, the weight of the charge and the time between two cuts.

4. Water Degradation Test

For each formulation, four normalized specimens (whose masses, dried at 103° C., were measured beforehand) are immersed in a tank of water (mineral water of *Cristalline* reference, Leclerc). The tanks are placed in a chamber heat-regulated at 32° C. and ventilated. A specimen is then withdrawn after 1, 2, 3 and 4 months and weighed (after oven treatment at 103° C. for 48 hours). The degradability of the material is measured by the loss of mass calculated in the following manner:

Loss (%)=(total loss of mass−loss of water 103° C.)×100

Results
1. Mechanical and Rheological Properties

The results obtained are presented in the table below:

TABLE 5

Properties of the materials

| Formulation (mass %) | Post-treatment | Resilience Kj/m² | MFR 150° C./2, 16 kg | Tensile tests ||||| Density (g/cm³) | % degradation at 3 months |
| | | | | Cmax TR MPa | Elongation at break (%) | Young's modulus (MPa) | Break at the end of traction | | |
|---|---|---|---|---|---|---|---|---|---|
| 100% CAPA | | 23 | 14 | 23 | 533 | 400 | No break | 1.11 | 1 |
| 98% CAPA + 2% lipase | | 24 | 14 | 23 | 530 | 450 | No break | 1.14 | 71 |
| 98% CAPA + 2% lipase | Storage for 1 month in the dark in a sealed bag | ND | ND | 26 | 530 | 500 | No break | 1.14 | 77 |
| 80% CAPA + 20% wheat | | 24 | 11 | 19 | 532 | 500 | No break | 1.16 | 18 |
| 55% CAPA + 45% wheat | | 21 | 4 | 9 | 286 | 675 | Break | 1.22 | 42 |

This table indicates that the addition of enzyme does not modify the mechanical properties of the CAPA tested here, namely the resilience, the MFR or the set of tensile parameters. This is in very marked contrast with the polymers consisting of 55% CAPA+45% wheat, for which all of the mechanical properties are degraded relative to CAPA alone. The mixture 80% CAPA+20% wheat itself makes it possible to conserve properties similar to that of CAPA alone.

Thus, the alloy of the invention is highly suited to improving the degradation of CAPA, while at the same time conserving its properties.

2. Degradation in Aqueous Media

The results indicate that CAPA alone is not degraded when it is immersed in an aqueous environment. If the addition of 20% of a plant-based charge makes it possible to improve the degradation of the alloy, it nevertheless remains that the maximum degree reached is less than 20%. As has already been indicated, this degradation corresponds to the degradation of the wheat flour, while the material itself remains unaltered.

An improvement in the biodegradation is thus directly correlated to an increase in the percentage of the plant-based charge in the alloy, with, as a corollary, impairment of the mechanical properties.

The results also indicate that the addition of enzymes is very much more advantageous than the addition of a plant-based charge, since it induces the degradation of CAPA (about 70% after 3 months in water), while at the same time conserving the mechanical properties of the pure material.

The inventors have thus succeeded in showing that the compositions obtained have better degradability than with a plant-based charge, while at the same time maintaining the mechanical properties of the polymer.

Finally, storage in the dark and in a sealed bag of the polymer 98% CAPA+2% lipase does not impair either the mechanical properties or its capacity to be degraded (comparison of the behavior of the polymers 98% CAPA+2% lipase optionally after post-treatment). The alloy of the invention is thus stable and is not degraded when it is not in solution and is thus suitable for storage.

In conclusion, the results as a whole indicate that the process for preparing polymer/enzyme alloys according to the invention is a particularly attractive industrial solution for the development of material with a short lifetime, while at the same time reducing the negative impacts on the environment that are inherent to the dissemination of residues into the natural medium.

Example 3

Impact of the Temperature on the Biodegradation of Polvcaprolactone (CAPA)

In order to demonstrate that the temperature of transformation of polycaprolactone has no impact on its biodegradation, polycaprolactone was extruded at 170° C. and its biodegradation was evaluated.

3.1. Step of Granulation by Extrusion of Polycaprolactone at 170° C.

The extrusion step is performed as defined in Example 1 (see the Materials and methods section 1), apart from the fact that the extrusion temperature in this example is 170° C. and the formulation is composed of 100% CAPA (without enzyme). The extrusion parameters are presented in Table 6.

TABLE 6

Parameters of the extrusion performed in this study

| Formulation | Extrusion temperatures (Zone 1 to die) | Speed BC 21, T/min | Pressure, bar | Torque (%) |
|---|---|---|---|---|
| 100 m % CAPA 6506 | 20-80-7*170 | 200 | 42 | 38 |

3.2. Injection Molding

The granules of 100% CAPA (cf. 100 m % CAPA 6506) then underwent an injection-molding step for the purpose of obtaining normalized specimens. The injection-molding step is performed as described in Example 1.

Table 7 presents the settings of the injection press that were used in this study.

TABLE 7

| Injection-molding parameters on an Arburg 100/420C/250 press | |
|---|---|
| Temperatures ° C. (Feed → Nozzle) | 40/55/60/80/100 |
| Imprint | Specimen |
| Assay speed (v401) m/min | 8.0 |
| Assay volume (V403) cm$^3$ | 19 |
| Counterpressure (p401) bar | 150 |
| Assay time (t402M) s | 4.5-7.5 |
| Injection pressure (p301) bar | 800 |
| Injection flow rate (Q301) cm$^3$/s | 5 |
| Switching (V311) cm$^3$ | 5 |
| Maintenance pressure (p321) bar | 650 |
| Maintenance flow rate (Q321) cm$^3$/s | 5 |
| Maintenance time (t321) s | 30 |
| Cooling time (t400) s | 20 |
| Cycle time (t902M) s | 60 |
| Mattress (V321I) s | 1 ± 0.5 |
| Ejector speed (v602) mm/s | 400 |
| Ejector force (F601) kN | 20 |
| Nozzle position | Detached |
| Mold temperature ° C. | Cold direct, 5° C. |

3.3. Measurement of the Biodegradation

Degradation in Water at 30° C.: Monitoring of the Loss of Mass

The degradation was evaluated in *Cristalline* mineral water. Four normalized specimens (whose masses were measured beforehand) were immersed in a tank of water. The tanks were then placed in a chamber heat-regulated at 32° C. and ventilated.

A specimen was then withdrawn after 15 days, 1, 2 and 3 months and weighed (after oven treatment at 103° C. for 48 hours). The degradability of the material was measured by means of the loss of mass, calculated as specified in Example 1.

As for the formulation 100 m % CAPA 6506 (see Example 2.), the "loss of mass" of the specimens prepared from the formulation 100 m % CAPA 6506-170 does not show any degradation after 2 months. The monitoring of the degradation in water at 32° C. makes it possible to demonstrate that CAPA alone does not degrade over time in water, when it is extruded at temperatures from 80° C. up to 170° C.

Example 4

Inclusion of 2% Lipase PS from *Pseudomonas cepacia* in 98% CAPA at 100° C.

4.1. Inclusion of the Enzyme

The inventors performed an extrusion of polycaprolactone incorporating said enzyme. To do this, a mixture of 98% by mass of polymer and 2% by mass of enzyme was placed in a metering device. The amounts used in the mixture are presented herein (see Table 8).

TABLE 8

| Formulation prepared in this study | | |
|---|---|---|
| Formulation (mass %) | Mass of enzyme (g) in metering device | Mass of CAPA 6506 P (g) in metering device |
| 98 m % CAPA 6506 + 2 m % lipase | 30 | 1500 |

4.1.a. Extrusion

The extrusion was performed at 100° C. The extrusion step was accomplished as described in Example 1 (see the Materials and methods section 1).

The extrusion parameters are presented in Table 9.

TABLE 9

| Parameters of the extrusion performed in this study | | | | |
|---|---|---|---|---|
| Formulation | Extrusion temperatures (Zone 1 to die) | Speed BC 21, T/min | Pressure, bar | Torque (%) |
| 98 m % CAPA 6506 + 2 m % lipase | 20-80-7*100 | 200 | 65 | 53 |

4.2. Injection Molding

The formulation then underwent a step of injection molding for the purpose of obtaining normalized specimens. The settings of the injection-molding press that were used in this study are the same as those used in Example 3 (see Table 7).

4.3. Biodegradation Measurement

The degradation efficacies were evaluated by degradation in water.

Degradation in Water at 30° C.: Monitoring of the Loss of Mass

The degradation was evaluated in *Cristalline* mineral water as in Example 3 (see section 3.3).

A specimen was then withdrawn after 15 days, 1, 2 and 3 months and weighed (after oven treatment at 103° C. for 48 hours). The degradability of the material was measured by means of the loss of mass, calculated as specified in Example 1.

The results obtained show a biodegradability with a loss of mass of 54% after 2 months. This demonstrates that the enzyme withstood the heat treatments inflicted during the extrusion and injection-molding steps.

The inventors have thus shown that an enzyme can effectively be incorporated into a polymer from the extrusion phase at 100° C. while at the same time conserving the degradation properties of the polymer.

Example 5

Inclusion of 2% Lipase PS into 98% CAPA at 120° C.

5.1. Inclusion of the Enzyme

The inventors performed an extrusion of polycaprolactone, incorporating said enzyme. To do this, the polymer was placed in one metering device and the enzyme in another, both being in powder form.

In the experiments that are presented here, the flow rates of these two metering devices were set so as to obtain a percentage of enzyme in the material of 2% (m/m) (see Table 10).

TABLE 10

| Formulation prepared in this study | | |
|---|---|---|
| Formulation (mass %) | Mass of enzyme (g) in metering device | Mass of CAPA 6506 P (g) in metering device |
| 98 m % CAPA 6506 + 2 m % lipase | 30 | 1500 |

5.1.a. Extrusion

The alloy between the polymer and the enzyme was prepared by extrusion at 120° C. The extrusion step was accomplished as described in Example 1 (see the Materials and methods section 1).

The extrusion parameters are presented in Table 11.

TABLE 11

Parameters of the extrusion performed in this study

| Formulation | Extrusion temperatures (Zone 1 to die) | Speed BC 21, T/min | Pressure, bar | Torque (%) |
|---|---|---|---|---|
| 98 m % CAPA 6506 + 2 m % lipase | 20-80-7*120 | 200 | 65 | 55 |

5.2. Injection Molding

The formulation was then subjected to an injection-molding step for the purpose of obtaining normalized specimens. The injection-molding conditions were identical to those of Example 3 (see Table 7).

5.3. Biodegradation Measurement

The degradation efficacies were evaluated by means of the degradation in water.

Degradation in Water at 30° C.: Monitoring of the Loss of Mass

The degradation was evaluated in water under the same conditions described in Example 3.

The results obtained show a biodegradability with a loss of mass of 27.5% after 2 months. This demonstrates that the enzyme withstood the heat treatments inflicted during the extrusion and injection-molding steps.

The inventors have thus shown that an enzyme can effectively be incorporated into a polymer from the extrusion phase at 120° C., while at the same time conserving the degradation properties of the polymer.

Example 6

Inclusion of 2% Lipase PS into 98% CAPA at 140° C.

The inventors performed an extrusion of polycaprolactone, incorporating said enzyme. To do this, the polymer was placed in one metering device and the enzyme in another, both being in powder form.

In the experiments that are presented here, the flow rates of these two metering devices were set so as to obtain a percentage of enzyme in the material of 2% (m/m) (see Table 12).

TABLE 12

Formulation prepared in this study

| Formulation (mass %) | Mass of enzyme (g) in metering device | Mass of CAPA 6506 P (g) in metering device |
|---|---|---|
| 98 m % CAPA 6506 + 2 m % lipase | 30 | 1500 |

6.1.a. Extrusion

The extrusion was performed at 140° C. The extrusion step was accomplished as described in Example 1 (see the Materials and methods section 1).

The extrusion parameters are presented in Table 13.

TABLE 13

Parameters of the extrusion performed in this study

| Formulation | Extrusion temperatures (Zone 1 to die) | Speed BC 21, T/min | Pressure, bar | Torque (%) |
|---|---|---|---|---|
| 98 m % CAPA 6506 + 2 m % lipase-140 | 20-80-7*140 | 200 | 59 | 48 |

6.2. Injection Molding

The formulation was then subjected to an injection-molding step for the purpose of obtaining normalized specimens. The settings of the injection-molding press that were used in this study are the same as those used in Example 3, section 3.2 (see Table 7).

6.3. Biodegradation Measurement

The degradation efficacies were evaluated by degradation in water.

Degradation in Water at 30° C.: Monitoring of the Loss of Mass

The degradation was evaluated in Cristalline mineral water as in Example 3 (see section 3.3).

A specimen was then withdrawn after 15 days, 1, 2 and 3 months and weighed (after oven treatment at 103° C. for 48 hours). The degradability of the material was measured by means of the loss of mass, calculated as specified in Example 1 (see the section Result 1.a.).

The results obtained show a biodegradability with a loss of mass of 4.5% after 2 months. This demonstrates that the enzyme withstood the heat treatments inflicted during the extrusion and injection-molding steps.

The inventors have thus shown that an enzyme can effectively be incorporated into a polymer from the extrusion phase at 140° C. while at the same time conserving the degradation properties of the polymer.

In conclusion, the inventors have illustrated that the process of the invention makes it possible to obtain a alloy that is degraded at various extrusion temperatures, in particular at 80° C., 100° C., 120° C. and 140° C.

Example 7

Methods for Introducing Lipase

In order to demonstrate the importance of the inclusion of lipase by extrusion on the biodegradation of the corresponding material, various methods for introducing lipase were performed on a polycaprolactone.

1: Introduction of Lipase by Extrusion (Test 7a)

A mixture of 98 m % polycaprolactone (CAPA 6506) and 2 m % lipase PS was extruded at 65° C. under the conditions described in Example 1 (see the Materials and methods section).

The extrusion parameters are presented in Table 14.

TABLE 14

Parameters of the extrusion performed in this study

| Formulation | Extrusion temperatures (Zone 1 to die) | Speed BC 21, T/min | Pressure, bar | Torque (%) |
|---|---|---|---|---|
| 98 m % CAPA 6506 + 2 m % lipase | 20-20-40-6*65 | 250 | 93 | 63 |

The formulation then underwent an injection-molding step for the purpose of obtaining normalized specimens. The settings of the injection-molding press are the same as those used in Example 3 (see Table 7).

The degradation efficacy of the injection-molded pieces was then evaluated by means of the degradation in water, according to the method described in Example 3.

2. Introduction of Lipase by Spraying onto the Surface of Infection-Molded Polycaprolactone Pieces (Test 7b)

A non-extruded polycaprolactone CAPA6506 underwent an injection-molding step for the purpose of obtaining normalized specimens. The settings of the injection-molding press are the same as those used in Example 3 (see Table 7).

An aqueous solution of lipase PS was then sprayed onto the surface of the injection-molded polycaprolactone pieces to obtain the equivalent of a mixture of 98 m % polycaprolactone and 2 m % lipase.

The degradation efficacy of the injection-molded pieces was then evaluated by means of the degradation in water, according to the method described in Example 3.

3. Introduction of Lipase into Water Used in the Test of Degradation in Water (Test 7c)

A non-extruded polycaprolactone CAPA6506 underwent an injection-molding step for the purpose of obtaining normalized specimens. The settings of the injection-molding press are the same as those used in Example 3 (see Table 7).

The degradation efficacy of the injection-molded pieces reference 7a was then evaluated by means of the degradation in water seeded with lipase PS, according to the method described in Example 3. The amount of lipase added is equivalent to a mixture of 98 m % polycaprolactone and 2 m % lipase PS.

The losses of mass of formulations 7a, 7b and 7c are collated in the table below:

TABLE 15

Loss of mass in water of samples 7a, 7b and 7c

| Reference | Lipase PS introduction method | Loss of mass (mass %) in water after | | | |
|---|---|---|---|---|---|
| | | 15 days | 1 month | 2 months | 3 months |
| 7a | Extrusion | 16 | 34 | 64 | 86 |
| 7b | Surface spraying | 17 | 21 | 21 | 21 |
| 7c | Seeding of the water used in degradation | 15 | 21 | 31 | 32 |

These results reveal the fact that when the lipase is introduced by spraying or into the degradation solution, the degradation is less substantial than when the lipase is included into the alloy.

In other words, the inventors have shown that the extrusion step makes it possible to obtain an alloy having better degradability than the step of dispersion/solution of the lipase.

Example 8

Additional Tests

The starting materials used for these additional tests are as follows:
polycaprolactone CAPA 6506;
wood flour Arbocel C320 supplied by Rettenmaier; and
La Dorée wheat flour supplied by AMO.

Various alloys of polycaprolactone, lipase PS and/or plant-based charge (wheat flour or wood flour) were prepared by extrusion under the conditions described in Example 1 (see the Materials and methods section):

TABLE 16

Composition of the various alloys obtained by extrusion in this study

| Reference | Composition |
|---|---|
| 7a | 98 m % CAPA + 2 m % lipase |
| 8 | 55 m % CAPA + 45 m % wood flour |
| 9 | 80 m % CAPA + 20 m % wood flour |
| 10 | 100% CAPA |
| 11 | 55 m % CAPA + 45 m % wood flour |

The extrusion parameters are presented in Table 17:

TABLE 17

Parameters of the extrusion performed in this study

| Extrusion temperatures (Zone 1 to die) | Speed BC 21, T/min |
|---|---|
| 20-20-40-6*65 | 250 |

The various alloys obtained were then subjected to an injection-molding step for the purpose of obtaining normalized specimens. The settings of the injection-molding press are the same as those used in Example 3 (see Table 7).

The degradation efficacies of the injection-molded pieces reference 7a, 8, 9, 10 and 11 were then evaluated by means of the degradation in water, according to the method described in Example 3. These efficacies are presented in the table below:

TABLE 18

Loss of mass of samples 7a, 8, 9, 10 and 11

| Reference | Composition | Loss of mass (mass %) in water after | | | |
|---|---|---|---|---|---|
| | | 15 days | 1 month | 1 months | 3 months |
| 7a | 98 m % CAPA + 2 m % lipase | 16 | 34 | 64 | 86 |
| 8 | 55 m % CAPA + 45 m % wheat flour | <1 | 3 | 6 | 9 |
| 9 | 80 m % CAPA + 20 m % wheat flour | <1 | 4 | 6 | 7 |
| 10 | 100% CAPA | <1 | <1 | <1 | <1 |
| 11 | 55 m % CAPA + 45 m % wood flour | <1 | <1 | <1 | <1 |

The inventors have thus shown that in order to obtain high biodegradability, the addition of enzymes is markedly more advantageous than the addition of a plant-based charge.

Example 9

Preparation of Polymer/Spore Alloy

1) Spore Productions
Spore Production Test MJ1

A 1 ml aliquot of *Bacillus licheniformis* from the culture collection was incubated in 100 ml of sterile nutrient broth (3 g of meat extract, 5 g of pepton and 2 g of glucose per liter) in a shaker incubator at 45° C. and 180 rpm for 31 hours. The culture was then transferred to a 5 liter fermentor filled with 2.9 liter of the same medium and grown at 45° C. under a 180 rpm stirring at a regulated pH of 6.8. After 143 hours of cultivation, sporulation was provoked by lowering pH to 4.4 while adding 30 ml of a 10 g/l manganese sulfate solution. Dry weight in the solution was estimated to 14.8 g/l as a result of 3 measurements without filtration. 50% of the bacteria were sporulated after 48 hours at 45° C. Spores were enumerated by the internally modified malachite green method.

Spore Production Test MJ2

A 2 ml aliquot of *Bacillus licheniformis* from the culture collection was cultivated in 200 ml of sterile nutrient broth (3 g of meat extract, 5 g of pepton and 2 g of glucose per liter) in a shaker incubator at 45° C. and 180 rpm for 29 hours and then transferred to a fermentor filled with 3.8 liter of the same medium and grown at 45° C. under a 180 rpm stirring at a regulated pH of 6.8. After 91 hours of culture, sporulation was provoked by lowering pH to 4.4 while adding 40 ml of a 10 g/l manganese sulfate solution. Dry weight in the solution was estimated to 10.8 g/l as a result of 5 pairs of measurements. As enumerated by the internally modified malachite green method, about 50% of the bacteria were sporulated after 72 hours at 45° C. The 4 liters thus produced were mixed with the 3 liters produced in the first production test. It was centrifuged to obtain a 2.4% w/w dry weight aqueous spore solution.

MJ1 and MJ2 solutions were then mixed together to obtain a bacterial solution MJ containing 2.4 weight percent of spore dry mater.

2) Extrusion Step 2 mixtures of polylactic acid PLA (recycled polylactic acid, Futuramat), wheat native flour (blé La Dorée®, AMO) and MJ solution were extruded into a co-rotating extruder Clextral BC21 (L=600 mm, L/d=24) with the following conditions:

Extrusion temperature zones: 20/80/140/170iso
Screw speed: 250 rmp
Torque: 40%
Internal pressure: 60-65 bar The compositions of the 2 materials were the following:
L22B07: 77.5 w % PLA+22.5 w % wheat native flour
SPLA01: 90.2 w % L22B07+9.8 w % MJ solution The compounds were dried in order to remove the residual water.

The two products obtained by granulation were injected into an Arburg 100T press so as to form specific specimens. The injection conditions are described in table 19 below:

TABLE 19

| Conditions of injection of the granulated products | | |
|---|---|---|
| | Injection 1 | Injection 2 |
| Reference | L22B07V01 | SPLA |
| Temperatures ° C. (Feed → Nozzle) | 130-145-155-165-170 | idem |
| Imprint | Multiple specimen | idem |
| Assay speed (v401) m/min | 25 | Idem |

TABLE 19-continued

| Conditions of injection of the granulated products | | |
|---|---|---|
| | Injection 1 | Injection 2 |
| Assay volume (V403) cm³ | 30 | 32.5 |
| Counterpressure (p401) bar | 150 | Idem |
| Assay time (t402M) s | 1.9 | about 3.5 |
| Injection pressure (p301) bar | 1750 | Idem |
| Injection flow rate (Q301) cm³/s | 10 | Idem |
| Switching (V311) cm³ | 5 | Idem |
| Maintenance pressure (p321) bar | 1650 | Idem |
| Maintenance flow rate (Q321) cm³/s | 10 | Idem |
| Maintenance time (t321) s | 20 | idem |
| Cooling time (t400) s | 20 | Idem |
| Cycle time (t902M) s | 48.6 | 40.9 |
| Mattress (V321I) s | 1.1 | Variable: 0.1 to 3.4 |
| Ejector speed (v602) mm/s | 50 | Idem |
| Ejector force (F601) kN | 110 | idem |
| Nozzle position | Detached after assay | Detached after assay |
| Mold temperature ° C. | 35 | 35 |
| Injectability (marked from A to D) | A | A |
| Color | light | dark |
| Aspect | A | A |
| Injected quantity | 40 | |
| Remarks | Silpack = 1 | Longer assay, irregular mattress |

3) Degradation Results

Degradation efficiencies were evaluated in Jolival water source. For each formulation, 4 specimens (initially weighted) were immersed in a water tank. The tanks were placed at 32° C. in a ventilated enclosure.

A sample was then taken after 1, 3, 6 and 9 months and weighed (after drying it at 103° C. for 48 h). Degradability was measured by mass loss.

TABLE 20

| Weight loss of polymer/spore alloys | | |
|---|---|---|
| Weight loss (w %) after x months of immersion | L22B07 | SPLA1 |
| 0 | 0 | 0 |
| 1 | 2.2 | 12.2 |
| 3 | 7.2 | 19.3 |
| 6 | 11.3 | 20.7 |
| 9 | 14.9 | 21.3 |

The introduction of spores into a PLA-based material is strongly increasing its degradability.

The invention claimed is:

1. A process for preparing a polylactic acid (PLA)/biological entities alloy, comprising:
    a step of selecting enzymes that degrade PLA; and
    a step of mixing said enzymes and PLA during extrusion at a temperature (T) corresponding to the melting point of PLA, the extrusion being performed in a twin screw extruder.

2. The process as claimed in claim 1, wherein the enzyme/PLA weight ratio is between about 0.1:100 and about 10:100.

3. A polymer/enzyme alloy made by the process as claimed in claim 1.

4. The process as claimed in claim 1, wherein the enzyme/PLA weight ratio is between about 1:100 and about 3:100.

5. The process as claimed in claim 1, wherein the enzyme/PLA weight ratio is about 2:100.

6. The process as claimed in claim 1, wherein the twin-screw extruder is a co-rotating extruder.

\* \* \* \* \*

UNITED STATES PATENT AND TRADEMARK OFFICE
CERTIFICATE OF CORRECTION

PATENT NO. : 10,829,598 B2
APPLICATION NO. : 15/220159
DATED : November 10, 2020
INVENTOR(S) : Thierry Ferreira et al.

Page 1 of 1

It is certified that error appears in the above-identified patent and that said Letters Patent is hereby corrected as shown below:

In the Specification

Column 5,
Line 5, "which makes make it" should read --which makes it--.

Column 18,
Line 36, "Polvcaprolactone" should read --Polycaprolactone--.

Column 23,
Line 10, "Infection-Molded" should read --Injection-Molded--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*